(12) United States Patent
Donnelly et al.

(10) Patent No.: US 6,921,024 B2
(45) Date of Patent: Jul. 26, 2005

(54) DISPOSABLE SHEET FRAGRANCE DELIVERY SYSTEM

(75) Inventors: Thomas E. Donnelly, Bedford, NH (US); Kristen A. Klett, Enfield, NH (US); Amy Suzanne Ebenezer, Westerville, OH (US); Renata Kvantas, Nashua, NH (US)

(73) Assignee: Alene Candles, Inc., Milford, NH (US)

( * ) Notice: Subject to any disclaimer, the term of this patent is extended or adjusted under 35 U.S.C. 154(b) by 0 days.

(21) Appl. No.: 10/355,592

(22) Filed: Jan. 31, 2003

(65) Prior Publication Data

US 2004/0149833 A1 Aug. 5, 2004

(51) Int. Cl.$^7$ .................... A24F 25/00; A01G 27/00; B05B 9/00; A61L 9/04
(52) U.S. Cl. .................... 239/44; 239/50; 239/53; 239/55; 239/145; 239/326
(58) Field of Search .................... 239/34, 41, 42, 239/44, 43, 50, 53, 55, 145, 326

(56) References Cited

U.S. PATENT DOCUMENTS

| | | | | |
|---|---|---|---|---|
| 604,562 A | * | 5/1898 | Evetts .................... 239/41 |
| 2,796,290 A | * | 6/1957 | Downs .................... 239/51.5 |
| 2,807,901 A | * | 10/1957 | Gilowitz .................... 239/49 |
| 3,441,353 A | * | 4/1969 | Claff .................... 401/132 |
| 3,868,052 A | * | 2/1975 | Rockefeller .................... 225/106 |
| 4,017,002 A | * | 4/1977 | Doyle et al. .................... 221/63 |
| 4,147,441 A | * | 4/1979 | Harrison et al. .................... 401/208 |
| 4,747,539 A | | 5/1988 | Spector |
| D305,865 S | | 2/1990 | Zutler |
| 4,913,349 A | | 4/1990 | Locko |
| 5,163,616 A | | 11/1992 | Bernarducci et al. |
| D354,224 S | | 1/1995 | Norton et al. |
| D354,225 S | | 1/1995 | Norton et al. |
| 5,560,514 A | * | 10/1996 | Frazier .................... 221/63 |
| 5,704,471 A | * | 1/1998 | Yamada .................... 206/207 |
| 5,718,353 A | | 2/1998 | Kanfer et al. |
| 5,832,648 A | * | 11/1998 | Malone .................... 43/1 |
| 5,875,968 A | * | 3/1999 | Miller et al. .................... 239/44 |
| 5,919,752 A | * | 7/1999 | Morelli et al. .................... 512/1 |
| D412,439 S | | 8/1999 | Cormack |
| D414,637 S | | 10/1999 | Amundson et al. |
| D416,794 S | | 11/1999 | Cormack |
| 6,138,867 A | | 10/2000 | Stelmack |
| 6,148,828 A | * | 11/2000 | Bourassa .................... 132/74.5 |
| 6,194,375 B1 | * | 2/2001 | Ness et al. .................... 512/4 |
| D450,960 S | | 11/2001 | Boyea et al. |
| 6,328,952 B1 | * | 12/2001 | Alboum et al. .................... 424/76.1 |
| 6,391,398 B1 | * | 5/2002 | Pesu et al. .................... 428/13 |
| 6,416,624 B1 | * | 7/2002 | Nielsen et al. .................... 162/155 |
| 6,429,261 B1 | * | 8/2002 | Lang et al. .................... 525/191 |
| 6,676,033 B1 | * | 1/2004 | Campesi, Sr. .................... 239/44 |
| 2002/0081930 A1 | * | 6/2002 | Jackson et al. .................... 442/416 |
| 2002/0155281 A1 | * | 10/2002 | Lang et al. .................... 428/337 |
| 2003/0091466 A1 | * | 5/2003 | Benko et al. .................... 422/5 |

FOREIGN PATENT DOCUMENTS

| | | |
|---|---|---|
| EP | 0 534 600 | 3/1993 |
| EP | 1 106 129 | 6/2001 |
| WO | WO 99/06311 | 2/1999 |
| WO | WO 01/74687 | 10/2001 |

* cited by examiner

*Primary Examiner*—William C. Doerrler
(74) *Attorney, Agent, or Firm*—Robert R. Deleault, Esq.; Mesmer & Deleault, PLLC

(57) ABSTRACT

A fragrance delivery system has an enclosure having a base and a top surface with a sheet dispensing outlet, a plurality of absorbent sheets disposed within the enclosure and configured for successive exposure of a portion of a sheet from the sheet dispensing outlet when a previous sheet is completely withdrawn from the enclosure. The fragrance delivery system also includes a quantity of fragrance solution within the enclosure and disposed about the plurality of sheets. The fragrance solution is formulated to vaporize into the air from the exposed portion of the sheet and the sheet dispensing outlet is sized to permit wicking of the fragrance solution up along the exposed portion of the sheet.

31 Claims, 5 Drawing Sheets

DISPOSABLE SHEET FRAGRANCE DELIVERY SYSTEM

BACKGROUND OF THE INVENTION

1. Field of the Invention

The present invention relates generally to room fragrance devices. Particularly, the present invention relates to passive room fragrance devices.

2. Description of the Prior Art

Fragrance devices are often used in the home and include fresh fragrant flowers and fruits. When fresh fragrant flowers and fruits are not in season, or not desired due to cost, pollen allergies, or other considerations, natural and manmade fragrance devices have been utilized. These fragrance devices include potpourri, candles, incense, perfumes, toilet waters, fragrant aerosol sprays and gel-type air fresheners.

Potpourri often contains a mixture of wood chips and dried flowers, fruits, leaves, nuts and the like that have either a natural fragrance or a fragrance imparted onto the mixture. In the home, the use of containers to hold colored and scented potpourri is well known. Potpourri, however, spills easily, gets dusty, degrades and generally becomes messy.

Candles, when burned, produce an aesthetic ambiance and a pleasant fragrance. Nevertheless, burning candles are unsuitable for use in homes with small children or pets where a lit candle can be accidentally knocked over causing burn injuries or resulting in a house fire. In addition, burning candles produce hot wax that can damage furniture or create injury. Likewise, incense must be burned in order to produce a scent. Burning incense, like a burning candle, can also be accidentally knocked over resulting in an increased risk of burn injuries or a house fire. Burning incense also produces messy ashes.

Aerosol perfumes, aerosol toilet waters and fragrant aerosol sprays of varying pleasant aromas are also well known to dispense a scent into a room. Aerosol particles dissipate into the air quickly, however, resulting in a need to spray the perfume, toilet water or other fragrant aerosol again and again at relatively short time intervals to maintain the desired level of fragrant scent.

Gel-type air fresheners are yet another type of air freshener. These are available in a passive configuration that sits on a shelf and in an active configuration that plug into an electrical outlet. This type of air freshener gives off a scent over a greater period of time. Even though improvements in the appearance of gel air fresheners have occurred, such air fresheners often have an industrial, unsightly appearance that detracts from a home's decor.

U.S. Pat. No. 4,747,539 (1988, Spector) discloses a reversible on-off fragrance emitting unit that is adapted to rest on a flat surface in either an upright or an upside down position. In one position, no fragrance is emitted. In the other position, a fragrance is emitted. The unit consists of a vented cylindrical shell closed at its upper end by a cover plate and at its lower end by a bottom wall. Disposed within the shell and secured to the cover plate is an absorbent pad. Joined to the pad is the leading end of a series of interhinged absorbent elements in an accordion formation. The trailing end of the series is joined to a weight whereby when the unit is upside down, the accordion is collapsed on the bottom wall and compressed by the overlying weight. When the unit is reversed in position and is made upright, the weight drops to the bottom wall, thereby expanding the accordion. The pad and the elements of the accordion are impregnated with a volatile fragrance, the pad acting as a reservoir therefor, whereby in the upside down position of the unit when the accordion is collapsed, no fragrance is emitted, and when in the upright position in which the accordion is expanded to expose the elements thereof, fragrance is emitted.

U.S. Pat. No. 4,913,349 (1990, Locko) discloses a device for dispensing volatile fragrances. The device comprises a hollow body and a liquid volatile fragrance contained within the hollow. The liquid volatile fragrance diffuses through a closure member made of a silicone rubber body to the outer surface where it is volatilized to disperse in the surrounding atmosphere.

U.S. Pat. No. 5,163,616 (1992, Bernarducci et al.) discloses an air freshener device with visual signal means. The air freshener device indicates when air freshening fragrance formulation contained therein is consumed. The device has a plurality of chambers which contain the same or different fragrance formulations. The inner walls of the chambers are contrastingly colored with respect to the fragrance formulation so that, when the fragrance formulation is consumed, the colored walls are exposed indicating to the user that the formulation within that chamber has been depleted. The multi-chamber feature of the device provides the possibility of multiple fragrance choices and, at the same time, allows for the release of fragrance for an extended period of time.

Sheet, or towelette, dispensers are commonly known in the field of personal hygiene. Personal hygiene sheet dispensers often contain combined dispensing and closure assemblies with sheet dispensing apertures designed and sized to prevent the protruding liquid-soaked sheet from drying out or from acting as a wicking component causing evaporation of the wet cleansing solution.

U.S. Pat. No. 6,138,867 (2000, Stelmack) discloses a towelette dispenser where the dispenser includes a closure having a well sized and shaped to receive and store a portion of a towelette extending out of the opening. The dispenser also includes a selectively movable cover having an opening defined therein that, when brought into alignment with the well, permits access to a towelette. When not in alignment, the movable cover establishes a substantially air-tight seal.

U.S. Pat. No. 5,718,353 (1998, Kanfer et al) discloses a towelette dispensing closure assembly for attachment to the lid of a container for the storage and dispensing of towelettes so as to be receivable within a preformed keyhole-shaped opening in the container lid. The assembly includes a body with a main radially extending flange larger than the opening in the lid. The lower portion of the body carries radially extending locking tabs which are dimensioned to fit through the lid opening and, upon the closure being turned, to engage the lower surface of the lid in opposed relationship with the flange which engages the upper surface. Antirotation tabs also extend radially of the lower portion of the body and again, upon rotation engages the edges of the lid opening to thus secure the closure on the lid. A cap is also provided to releasably engage the upper portion of the closure body to provide a substantially airtight seal for the container.

U.S. Pat. No. 5,560,514 (1996, Frazier) discloses a wet wipe dispensing nozzle with rotatable port. The centerflow dispenser includes a dispensing nozzle affixed to the container of wet wipes. The nozzle has a rotatable dispensing disk with dispensing orifice therethrough which includes a node and a plurality of contiguous appendages such that the disk will rotate to the path of least resistance as the saturated wipers are drawn through the dispensing orifice regardless of the direction of extraction through the orifice. One or more drain holes are provided through the dispensing disk to allow liquid squeezed from the wiper as it is drawn through the dispensing orifice to pass back into the container. The nozzle includes a funneled section which collects any liquid squeezed or which may drip from the wipe as it is extracted from the container and directs that liquid toward the drain holes in the dispensing disk. A cap is provided which sealingly engages the nozzle to limit vapor emissions from the container when the cap is in the closed position.

International Publication No. WO 01/74687 A1 (2001, Buck et al.) discloses a wet wipe container with flexible orifice so that a user may reach through the slits to grasp a wet wipe in the event that the pop up feature fails. Further, the nature of the flexible, rubber-like material or sheet having the slits must, among other things, be sufficiently stiff to maintain a reasonable impediment against evaporation losses and to hold the wet wipes in the pop-up position.

It should be understood that the cleansing liquids used in wet wipes generally consist of water and alcohol in order to enhance evaporation of the liquid in a relatively short time period after a wet wipe is used. This formulation is the reason the prior art is concerned with the use of airtight seals to prevent evaporation of the liquid in the wet wipe container.

Therefore, what is needed is a fragrance dispenser system that allows dispensing of a room fragrance at a variable rate. What is also needed is a fragrance dispenser system that is a passive fragrance dispenser that uses a plurality of separable sheets. What is further needed is a fragrance dispenser system that can be used as a drawer or closet fragrance applicator. What is still further needed is a fragrance dispenser that can be used as a personal fragrance applicator. What is yet further needed is an aesthetically pleasing fragrance dispenser system that complements the decor of a room.

SUMMARY OF THE INVENTION

It is an object of the present invention to provide a passive room fragrance dispenser system that is easily renewed at a given time interval without replacing the core fragrance-producing component. It is another object of the present invention to provide a fragrance dispenser system that can dispense a fragrance at a variable rate. It is also an object of the present invention to provide a room fragrance dispenser system that does not require an open flame. It is still another object of the present invention to be outwardly decorable to reduce the industrial appearance of the device. It is a further object of the present invention to be readily insertable into an aesthetically pleasing home decor container to further reduce the industrial appearance of the device. It is yet another object of the present invention to provide a fragrance dispensing system that can be secondarily used as a personal fragrance applicator. It is yet another object of the present invention to provide a fragrance dispensing system that can be secondarily used as a drawer or closet fragrance applicator. It is still yet another object of the present invention to provide a fragrance dispensing system that can be secondarily used as a garbage receptacle fragrance applicator.

The present invention achieves these and other objectives by providing a disposable sheet fragrance delivery system having an enclosure, a plurality of dispensable sheets, a quantity of fragrance solution, and a sheet dispensing outlet. A sheet dispensing outlet cover may optionally be provided.

The enclosure has a main body, a bottom and a top. The enclosure can be of any size or shape, but is typically less than twelve inches in height and twelve inches in diameter. The container exterior may be made of any waterproof natural or manmade material such as glass, ceramic, plastic, metal, composites, and the like. The top or bottom of the container may be made of a different material than the body of the container. The top or the outside surface of the container may contain decoratively-shaped openings to increase the dissipation of the fragrance solution into the air. The container may be aesthetically decorated to stand alone in a room. External finishes, such as frosted, painted, jeweled or labeled finishes may be applied to the stand-alone container. The fragrance container may also be adaptably shaped for further insertion into a corresponding home decor container of varying size, shape, or color.

The top of the enclosure houses the sheet dispensing outlet. The size of the sheet dispensing outlet is one of several factors that is critical to the present invention's ability to dispense a room fragrance. Unlike the sheet dispensing openings of a cleaning towelette dispenser that are designed to limit the evaporation of the highly volatile cleaning solution and the wicking action of the towelette, the sheet dispensing outlet of the present invention is sized to allow and to enhance the dissipation of the fragrance solution from the container preferably through the wicking action of the dispensable sheet. The shape of the opening is not critical, only its size.

The plurality of dispensable sheets has a structure that permits capillary action. Sheets of the present invention are preferably made of an airlaid, nonwoven substrate. A nonwoven substrate is a fabric consisting of an assembly of textile fibers such as wood pulp, rayon, polyester fibers, and the like, that are oriented in one direction or in a random manner. They are typically held together by mechanical interlocking, by fusing of thermoplastic fibers, or by bonding with a rubber, starch, glue, casein, latex, or a cellulose derivative or synthetic resin. Airlaying is a technique of dispersing fibers in a moving airstream and then collecting them on a forming surface to produce lofty, porous webs. Airlaid fabrics are very absorbent, yet lightweight.

The plurality of sheets may be rolled and perforated or otherwise separably stacked to allow for insertion of a portion of a single sheet through the sheet dispensing outlet. The sheets are typically less than twelve inches by twelve inches. The sheets may be dyed with a color to correspond with the scent of the fragrance solution. The sheet roll or stack may either be saturated with fragrance solution before placement into the container or the fragrance solution may be dispensed onto the sheet roll or stack after placement into the container until the saturation point of the sheet substrate is reached.

The fragrance solution is another important factor in the functioning of the present invention. Unlike the cleaning solutions used in the towelette dispenser systems, the fragrance solution of the present invention is specially formulated to provide the ability to dispense an aromatic scent into a room or within a given area. The fragrance solution is a water-based formula containing fragrance dispersion agents and a fragrance oil. Specifically, the fragrance solution contains water, a stabilizer, a quantity of fragrance, a solvent, a light stabilizer, a buffer, a preservative, and an antioxidant. Where the fragrance sheet is to serve double-duty as a cleaning sheet/wipe in addition to a room fragrance sheet, a chelating agent and a foaming agent may be added to the fragrance solution.

The present invention's unique combination of sheet dispenser with a critically-sized sheet dispensing outlet and the specially formulated fragrance solution provides a new and previously unknown disposable sheet fragrance delivery system. The present invention takes advantage of the capillary action of the fragrance solution on the substrate sheet roll or stack. The capillary action begins in the base of the container where the fragrance solution permeates the base of the sheet roll or stack and moves upward through the sheet roll or stack toward the sheet that protrudes outward through the sheet dispensing outlet. A desired amount of sheet material is exposed to the air.

The sheet dispensing outlet is sized so that, once the fragrance solution has permeated the protruding sheet, the fragrance is dissipated into the air within the room. To increase the amount of fragrance within a room, a user may pull up on the protruding sheet to increase its exposed length out of the dispenser, thus increasing the fragrance in the room. The exposed length may be increased again and again until the exposed fragrance sheet is entirely separated from the plurality of sheets within the container and removed from the container. Typically, the fragrance solution formulation and the size of the sheet are configured to be used for a period of about twenty-four hours. At which time, the sheet is removed and the next sheet is exposed to the air, rejuvenating the fragrance dispersion level. It should be noted that if the sheet is not removed, the capillary action of the fragrance solution up the sheet will continue to disperse fragrance into the air.

Once removed from the container, the fragrance sheet may be placed in a drawer to impart fragrance into the drawer, hung over a hanger in a closet to impart fragrance into the closet, or placed in a trash receptacle to impart fragrance into the receptacle. The removed fragrance sheet may also be used as a fragrance wipe to impart a fragrance to the user's body.

A cap may be optionally provided with the fragrance dispensing system and may optionally be attached to the container or to the sheet dispensing outlet to prevent removal of additional fragrance sheets and continuing loss of fragrance solution in the event that the fragrance dispensing system is stored.

Multiple rolls or stacks of sheets may be placed into a compartmentalized container with an enlarged diameter, a corresponding multiple quantity of fragrance solution, and corresponding multiples of sheet dispensing outlets to impart fragrance into rooms of greater size. Alternatively, each compartment may contain a different fragrance-bearing formulation providing the user an option to select the fragrance sheets and the fragrance the user wishes to diffuse into the room.

DETAILED DESCRIPTION OF THE PREFERRED EMBODIMENT

Figure 1:
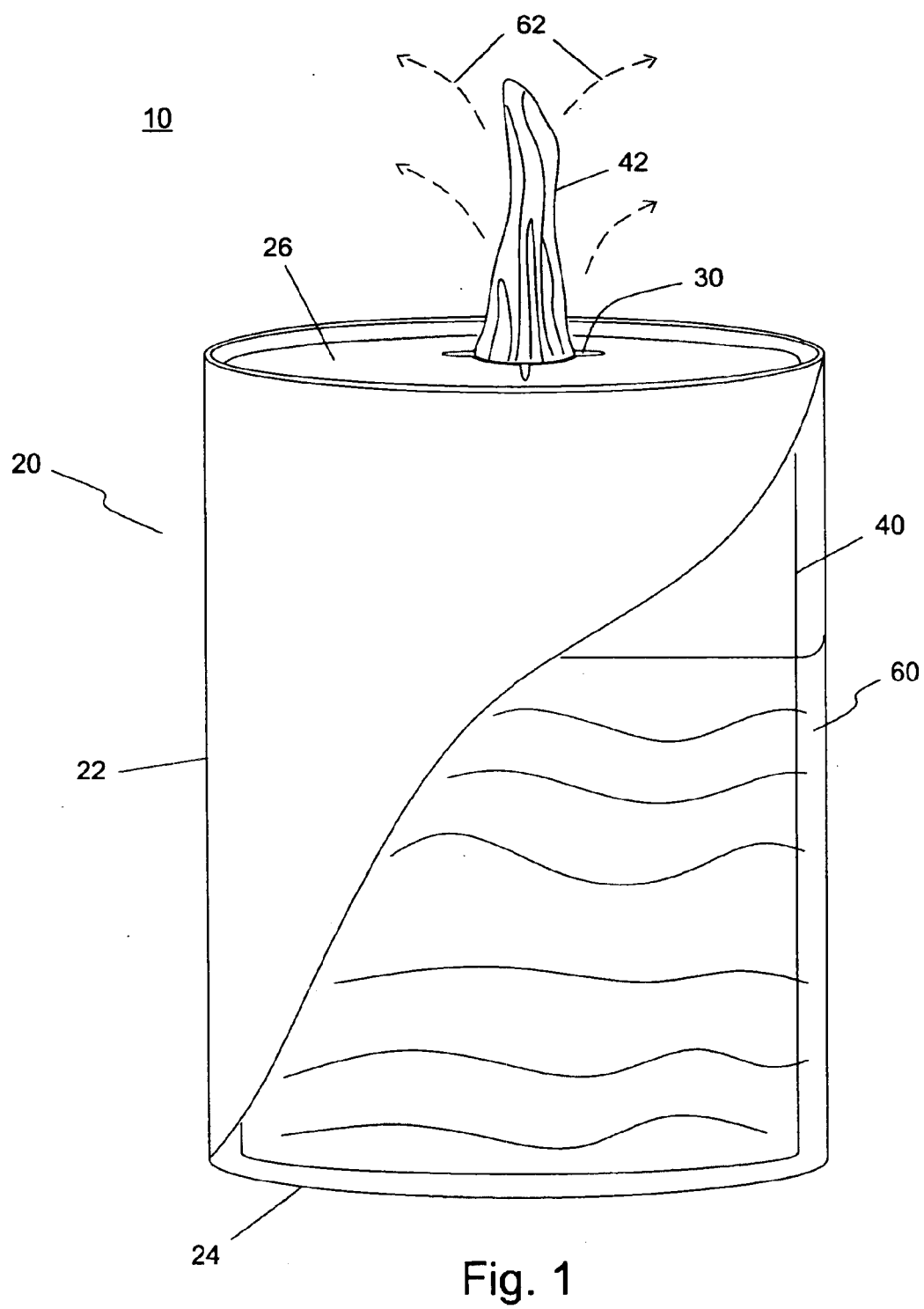
FIG. 1 is a partial cut-away view of one embodiment of the room fragrance system of the present invention.

The preferred embodiment of the present invention is illustrated in FIGS. 1–5. FIG. 1 shows the fragrance sheet dispenser system 10 of the present invention. Fragrance dispenser system 10 includes an enclosure 20, a plurality of sheets 40 and a fragrance solution 60. A portion 42 of one of the plurality of sheets 40 is shown protruding from sheet outlet 30. Arrows 62 illustrate the dispersion of fragrance into the air.

Enclosure 20 has a main body 22, a bottom 24 and a top 26. Top 26 may be a separate removable cover or it may be permanently fixed to main body 22. Whether removable or not, top 26 includes a sheet dispensing outlet 30 through which each subsequent sheet is pulled by the user. Enclosure 20 can be any size or shape but is preferably at least three inches tall but less than twelve inches in height and twelve inches in diameter. Enclosure 20 may be made of any waterproof material, either natural or manmade, such as glass, ceramic, plastic, metal, composites, and the like. It should be understood that top 26 or bottom 24 may be made of a different material than body 22. Top 26 or a portion of body 22 adjacent top 26 may optionally include decoratively-shaped openings to increase the dissipation of the fragrance solution into the air. Optional external finishes may be applied to the outside surface of enclosure 20. Examples of such external finishes include frosted, painted, jeweled, or labeled finishes.

Figure 2A:
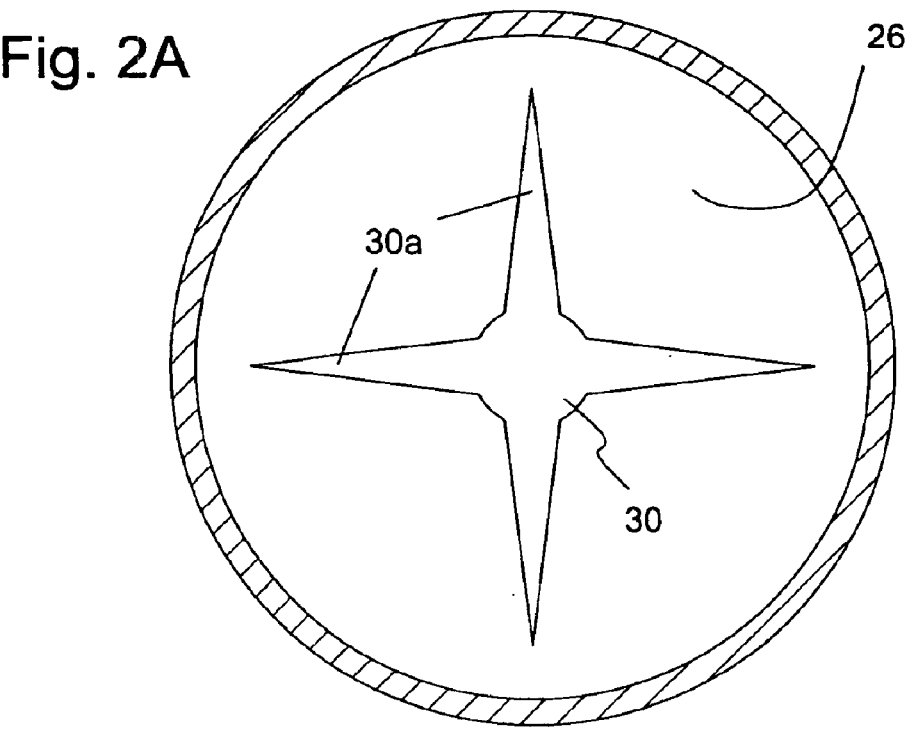
FIGS. 2A and 2B are top views of useable sheet dispensing openings of the present invention.
Figure 2B:
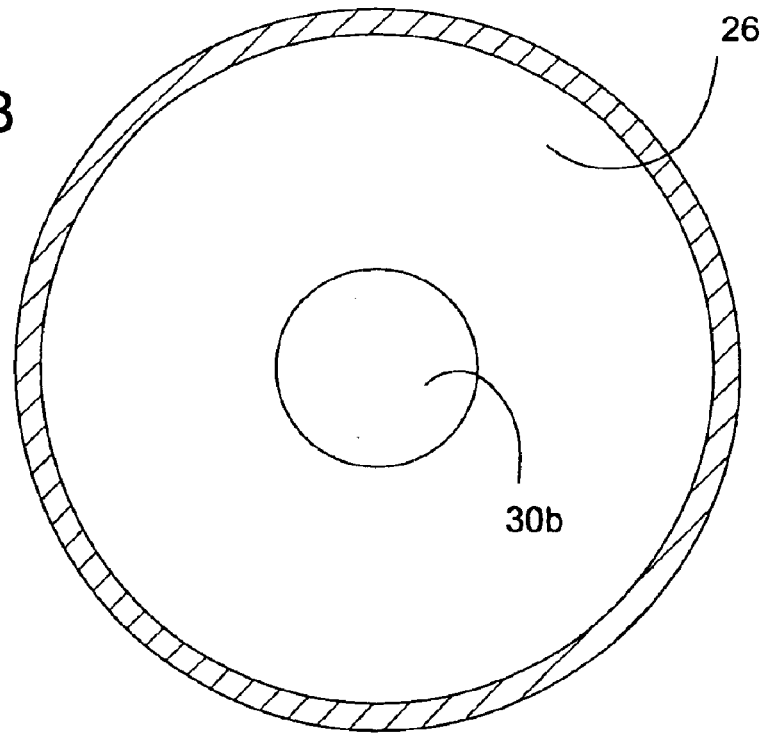

Top 26 includes sheet dispenser outlet 30. Turning now to FIGS. 2A and 2B, there is shown two embodiments of sheet dispenser outlet 30. FIG. 2A includes a central, circular opening with four, equally-spaced elongated openings 30a through which a single sheet is withdrawn. FIG. 2B includes a central circular opening 30b through which a single sheet is withdrawn. Although the shape of the outlet 30 is not critical, the cross-sectional area of the opening is critical. For the present invention to function as a fragrance delivery system, it is important to have a cross-sectional area of about 0.19 square inches or larger.

Figure 3:
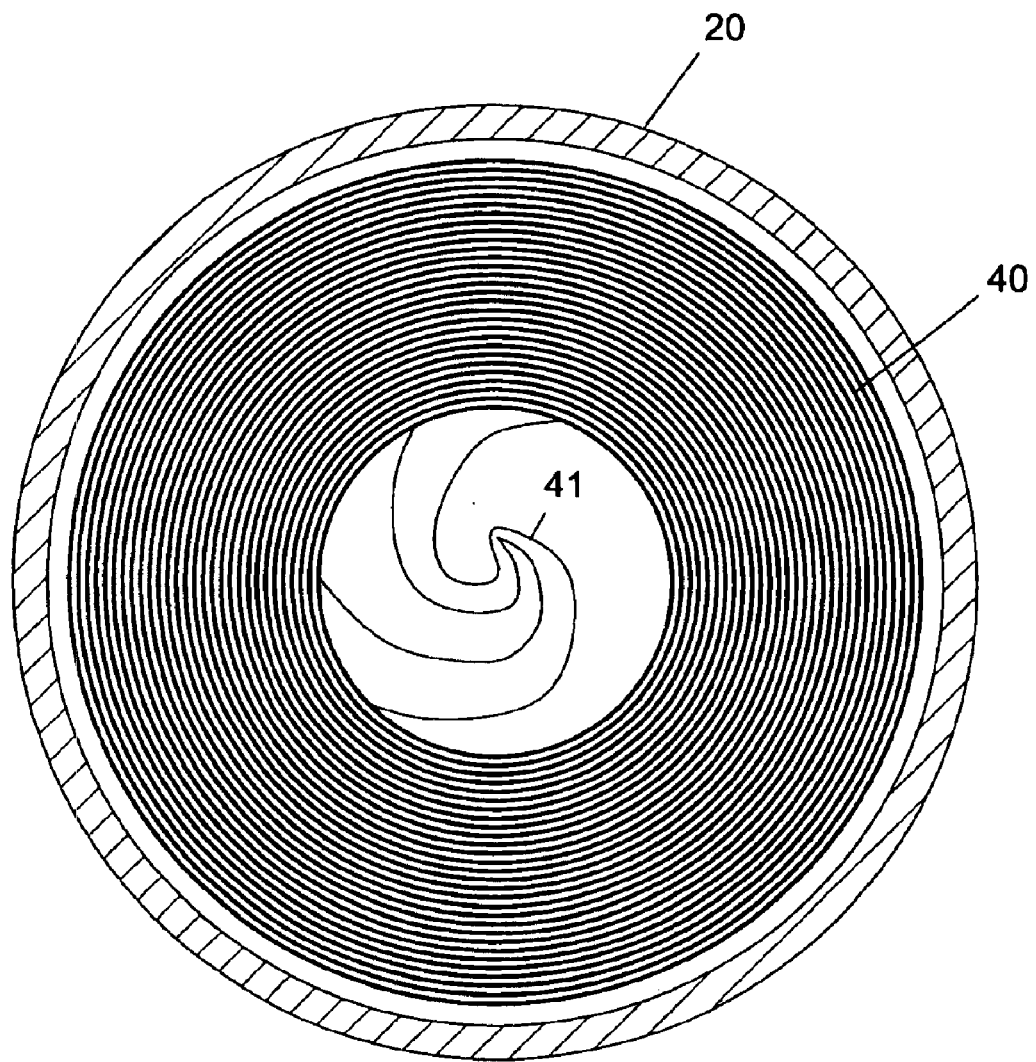
FIG. 3 is a cross-sectional view along the width of the embodiment in FIG. 1.

FIG. 3 shows a cross-sectional view of the embodiment in FIG. 1. Within enclosure 20, there is a plurality of disposable fragrance sheets 40 configured into a roll. Each sheet is partially separated from adjacent sheets with perforations (not shown) and the plurality of sheets is preferably of equal size. Each sheet is pulled from the center of the roll of sheets as indicated by sheet 41.

The substrate used as the plurality of sheets 40 is an airlaid, nonwoven material that may be made from materials such as wood pulp, rayon, and/or polyester fibers. The fibers may be oriented in one direction or in a random manner. The plurality of sheets 40 may be optionally dyed with a color to correspond to the scent of the fragrance solution.

Figure 4:
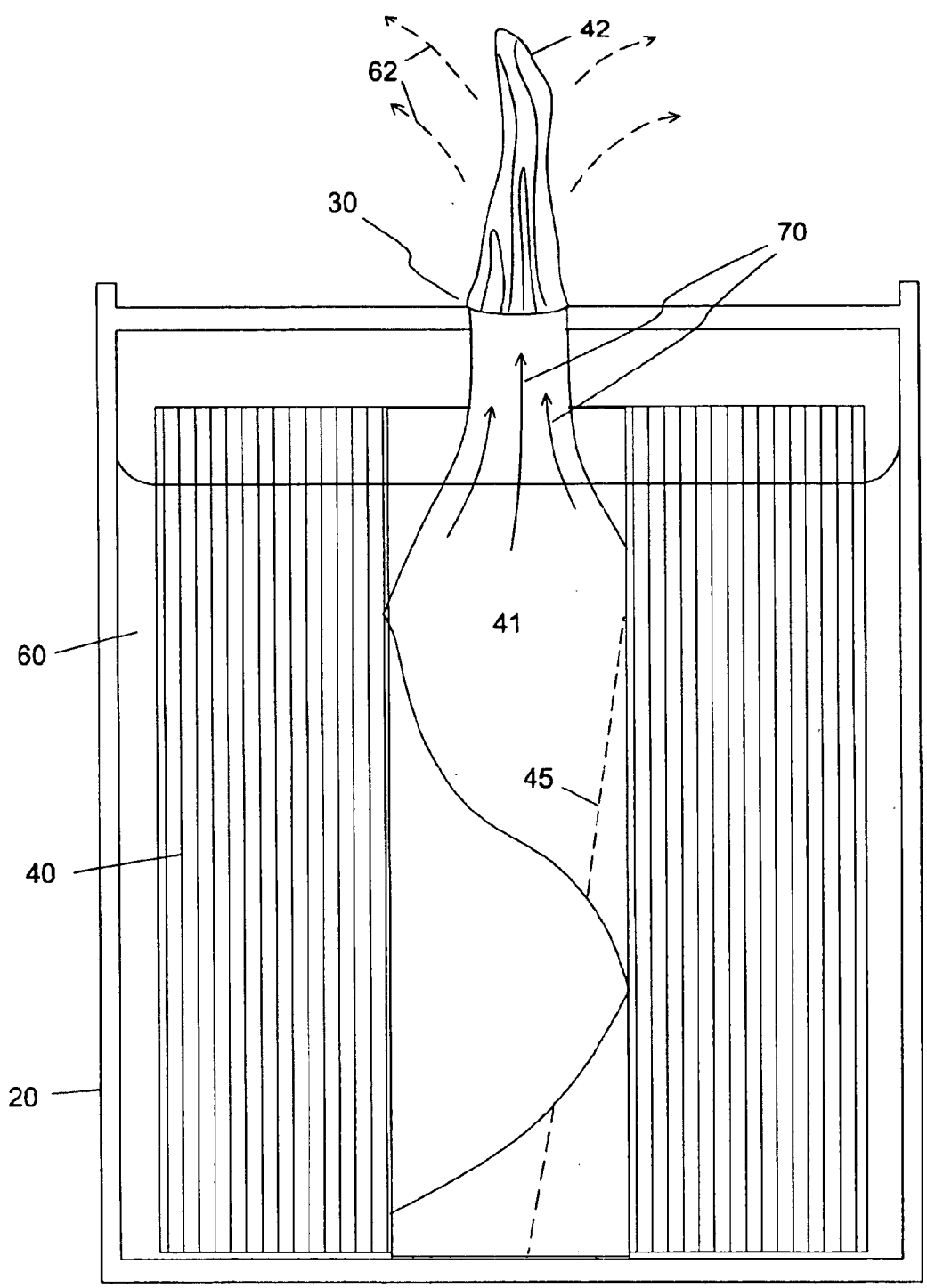
FIG. 4 is a cross-sectional view along the length of the embodiment in FIG. 1.

Turning now to FIG. 4, there is illustrated a cross-sectional view of the present invention along its length. In this embodiment, the plurality of fragrance sheets 40 is in a roll where each sheet is withdrawn from enclosure 20 from the center of the roll. Sheet 41 is a representation of a fragrance sheet with perforations 45 that has a portion 42 extending from sheet dispensing outlet 30. The plurality of sheets 40 are immersed in a fragrance solution 60. Arrows 70 illustrate the capillary action of fragrance solution 60 up along fragrance sheet 41 to portion 42 where fragrance solution 60 then diffuses into the air as represented by arrows 62.

Fragrance solution 60 is composed of is a water-based formulation containing fragrance dispersion agents and a fragrance. In the present invention, the fragrance solution contains water, a stabilizer, a quantity of fragrance, a solvent, a light stabilizer, a buffer, a preservative, and an antioxidant. The water used in making fragrance solution 60 is tap water, and preferably deionized water. Typically, water makes up about 15–70% of the solution, and preferably from about 20–60%.

Various surfactants may be used in fragrance solution 60. Examples of acceptable surfactants are hydrotrope, sodium xylenesulphonate, dimethlbenzenesulfonic acid sodium salt, Conco SXS, Cyclophil SXS30, Eltesol SX30, Naxonate, Surco SXS, Ultrawet 40 SX, Calsoft SXS96, Alkatrope SX40, Carsoslf SXS, Eltesol SX93, Reworil NXS40, Richonate SXS, polyethylene glycol p-tert-octylphenyl ether, Triton X114, Witconate SXS, sodium sulfate, disodium sulfate, Triton 102, alpha-[(1,1,3,3-tetramethylbutyl)phenyl]-omega-hydroxypoly(oxy-1,2-ethanediyl), Bio-Terge, Amphosol, Betaine, trimethylammonioacetate, methnaminuim, Stepanol, steols, Bio-Soft, Marprosyl, sulfosuccinates, and sodium xylenesulfonate. The preferred surfactant is sodium xylenesulfonate and is available under the trademark Stepanate SXS from the Stepan Company of Northfield, Ill. Typically, the surfactant is present in the range of about 25% to about 75%, but preferably in the range of about 35% to about 65%.

The fragrance is typically obtained from a fragrance supplier. For use in the present invention, the fragrance must be water-soluble. When the fragrance obtained is not water soluble, surfactants may be used to solubilize the oil-based fragrance into an aqueous solution. All as is well known by those of ordinary skill in the art. There are various fragrance suppliers known to those skilled in the art such as, for example, AromaTech of Sommerville, N.J., Noville of South Hackensack, N.J., Belmay, Inc. of Yonkers, N.Y., Wessel Fragrances of Elmwood, N.J., etc. The fragrance oil is typically present in the range of about 3% to about 22%, preferably in the range of about 4% to about 18% but most preferably in the range of about 5% to about 10%.

The solvent is typically in the range of about 1% to about 20%. Preferably, the solvent is in the range of about 2% to about 10%. Examples of acceptable solvents are dipropylene glycol, butylene glycol, hexylene glycol, propylene glycol, isopropanol, dipentene, 3-methoxy-3-methyl-1-butanol, limonene, and benzyl benzoate. The preferred solvent is dipropylene glycol, which is available from various suppliers such as, for example, BASF Corporation, Dow Chemical, KIC Chemicals, Inc., to name a few.

The light stabilizer concentration is in the range of about 0.0001% to about 0.05%, but preferably in the range of about 0.005% to about 0.01%. Examples of acceptable light stabilizers are octyl methoxycinnamate, benzophenone and benzotriazole derivatives. The preferred light stabilizer is a benzotriazole derivative available under the trademark TINOGARD™ APA from Ciba Specialty Chemicals.

A buffer is added to the solution in the range of about 0.0% to about 1.2%. The preferred range is about 0.0% to about 0.05%. Buffers such as, for example, lactic acid, hydrochloric acid, phosphoric acid, stearic acid, sulfuric acid, and citric acid may be used. The preferred buffer for the present invention is citric acid. Citric acid may be obtained from a variety of suppliers including, but not limited to, Alfa Chem, Ameresco, Inc. Asiamerica International, Inc., Dastech International, Inc., Evergreen Corporation, Roche Vitamins, Inc., etc.

The preservative in fragrance solution 60 is typically in the range of about 0.001% to about 1.1%, and preferably in the range of about 0.005% to about 1%. Examples of acceptable preservatives are benzoic acid, methylparaben, ethylparaben, propylparaben, alcohol SD40, alcohol SDA39-C-190, ethyl alcohol, triclosan, triclocarbon, phenoxyethanol, sodium hydroxymethylglycinate, and germaben. Sodium hydroxymethylglycinate available under the tradename SUTTOCIDE™ A from ISP Technologies, Inc. of Wayne, N.J., is the preferred preservative.

An antioxidant is also included in fragrance solution 60 in the range of about 0.0% to about 0.1%, and preferably in the range of about 0.0% to about 0.05%. Butylated hydroxyanisol, tocopheryl acetate, vitamin E, and butylated hydroxytoluene are examples of acceptable antioxidants for use in the present invention. The preferred antioxidant is butylated hydroxytoluene. Butylated hydroxytoluene is readily available from suppliers such as, for example, Alfa Chem, Eastman Chemical Company, Shell Chemical Company, Spectrum Chemical Mfg. Co., etc.

In another embodiment of the fragrance solution 60 of the present invention, the fragrance solution 60 may be formulated to serve double-duty as a cleaning sheet/wipe in addition to a room fragrance sheet. In this other embodiment, fragrance solution 60 may include in addition to the above-described components, a chelating agent and a foaming agent. Both the chelating agent and the foaming agent are typically present in the range of about 0% to about 15%, but preferably in the range of about 0% to about 10%. Depending on the fragrance oil used and the concentration of the other ingredients, a chelating agent and/or a foaming agent may not be required. Further, a disinfecting agent in the range of about 0.01% to about 15%, preferably in the range of about 1% to about 10%, may also be added to the fragrance solution.

Examples of acceptable chelating agents include tetrasodium ethylenediaminetetraacetate, (ethylenedinitrilo) tetraacetic acid tetrasodium salt, disodium ethylenediaminediacetate, trisodium ethylenediaminetriacetate, trisodium nitrilotriacetate, sodium hydroxide, sodium glycolate, and versene. The preferred chelating agent is versene.

Examples of acceptable foaming agents include diolamine, alkanolamide, diethanolamine, iminodiethanol, diethylolamine, bis-(2-hydroxyethyl)amine, ninol, cocoamide, and ammonyx. The preferred foaming agent is diethanolamine.

Dyes may be added to fragrance solution 60 to match the color implied by the scent of the fragrance oil used. For example, adding an orange dye to fragrance solution 60 when orange-scented fragrance oil is used.

Figure 5:
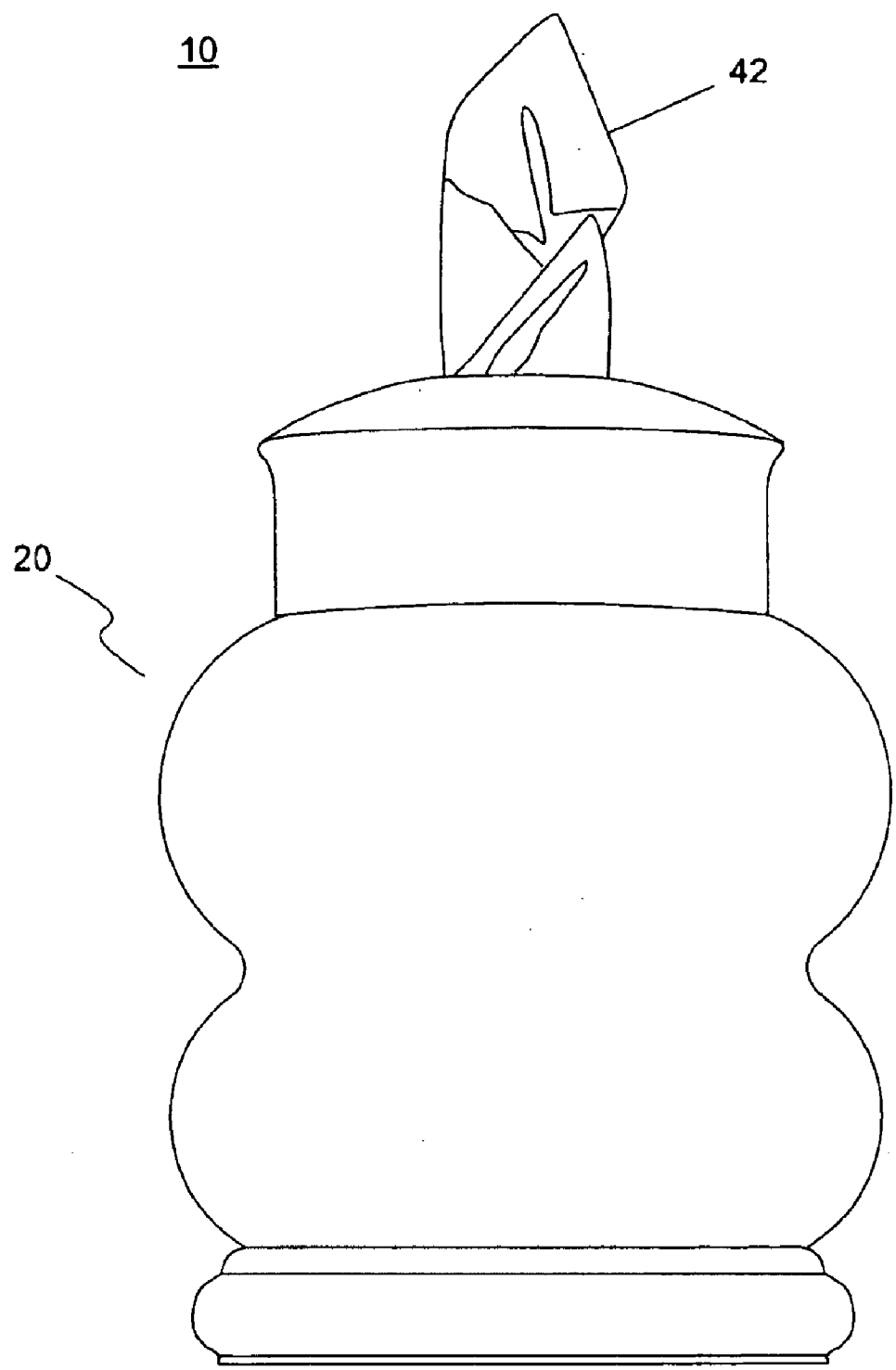
FIG. 5 is a side view of another embodiment of the present invention.

Turning now to FIG. 5, there is illustrated an example of another embodiment of the enclosure 20. In this embodiment, enclosure 20 is a decoratively shaped container that may also included an external finish such as frosted, painted, jeweled, or labeled finish. Enclosure 20 may also have any shape to match the home décor. In addition to forming enclosure 20 into an aesthetically decorated container, enclosure 20 may also be configured as a replaceable insert that can be added to a decorative holder. In such a case, a disposable sheet fragrance kit can be provided that includes a decorative container with one or more replacement disposable sheet fragrance inserts. This allows the user to refill a decorative container or holder that the user does not wish to throw away.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A fragrance delivery system comprising:
   an enclosure having a base and a top surface with a sheet dispensing outlet;
   a plurality of absorbent sheets disposed within said enclosure and configured for successive exposure of a portion of a sheet from said sheet dispensing outlet when a previous sheet is completely withdrawn from said enclosure; and
   a quantity of fragrance solution within said enclosure and disposed about said plurality of sheets, said fragrance solution being a mixture of water in a range of about 15 percent to about 70 percent, a surfactant in a range of about 25 percent to about 75 percent, a fragrance in a range of about 3 percent to about 22 percent, a solvent in a range of about 1 percent to about 20 percent, a light stabilizer in a range of about 0.0001 percent to about 0.05 percent, a buffer in a range of greater than 0.0 percent to about 1.2 percent, and a preservative in a range of about 0.001 percent to about 1.1 percent, said fragrance solution formulated to vaporize into the air from said exposed portion of said sheet and wherein said sheet dispensing outlet is sized to support one of said plurality of absorbent sheets and to permit wicking of said fragrance solution up along said exposed portion of said sheet.

2. The fragrance delivery system of claim 1 wherein said outlet has a cross-sectional area of about 1.19 square inches or greater.

3. The fragrance delivery system of claim 1 wherein said enclosure is made of a waterproof material.

4. The fragrance delivery system of claim 1 wherein said plurality of absorbent sheets are made of a nonwoven, airlaid material.

5. The fragrance delivery system of claim 1 wherein said plurality of sheets are separated from each other by perforations.

6. The fragrance delivery system of claim 1 wherein said plurality of sheets are interleaved.

7. The fragrance delivery system of claim 1 wherein said plurality of sheets are a continuous roll.

8. The fragrance delivery system of claim 1 wherein said fragrance solution further includes an antioxidant.

9. The fragrance delivery system of claim 1 wherein said fragrance solution contains said water in a range of about 20 percent to about 80 percent, said surfactant in a range of about 35 percent to about 65 percent, said fragrance in a range of about 4 percent to about 18 percent, said solvent in a range of about 2 percent to about 10 percent, said light stabilizer in a range at about 0.005 percent to about 0.01 percent, said buffer in a range of greater than 0.0 percent to about 0.05 percent, said preservative in a range of about 0.005 percent to about 1 percent.

10. The fragrance delivery system of claim 1 wherein said fragrance solution further includes an antioxidant in the range of greater than 0.0 percent to about 0.1 percent.

11. The fragrance delivery system of claim 9 wherein said fragrance solution further includes and antioxidant in the range of greater than 0.0 percent to about 0.05 percent.

12. The fragrance, delivery system of claim 1 wherein said fragrance solution further includes a chelating agent.

13. The fragrance delivery system of claim 12 wherein said chelating agent is in the range of greater than zero percent but less than or equal to a range of about 15 percent.

14. The fragrance delivery system of claim 13 wherein said chelating agent is in the range of greater than zero percent but less than or equal to a range of about 10 percent.

15. The fragrance delivery system of claim 1 wherein said fragrance solution further includes a foaming agent.

16. The fragrance delivery system of claim 15 wherein said foaming agent is in the range of greater than zero percent but less than or equal to a range of about 15 percent.

17. The fragrance delivery system of claim 16 wherein said foaming agent is in the range of greater than zero percent but less than or equal to a range of about 10 percent.

18. The fragrance delivery system of claim 1 wherein said delivery system further includes a decorative holder for receiving said enclosure.

19. A method of radiating a fragrance from a fragrance delivery system, said method comprising:
   formulating at least one air fragrance solution to contain a mixture of in a range of about 15 percent to about 70 percent, a surfactant in a range of about 25 percent to about 75 percent, a fragrance in a range of about 3 percent to about 22 percent a solvent in a range of about 1 percent to about 20 percent, a light stabilizer in a range of about 0.0001 percent to about 0.05 percent, a buffer in a range of greater than 0.0 percent to about 1.2 percent, and a preservative in a range of about 0.001 percent to about 1.1 percent;
   containing said at least one air freshening fragrance solution and a plurality of absorbent sheets in an enclosure having a top outlet wherein said top outlet has an opening sized to support one of said plurality of absorbent sheets and to allow said fragrance solution to permeate from said fragrance delivery system through an exposed portion of one of said plurality of absorbent sheets to said environment; and
   withdrawing a portion of a single sheet of said plurality of absorbent sheets out of said top outlet to connect said fragrance solution with atmosphere to allow said fragrance solution to wick up said sheet and to dissipate into the environment.

20. The method of claim 19 further comprising removing said single sheet from said outlet to expose another portion of a second sheet of said plurality of absorbent sheets.

21. The method of claim 19 further comprising formulating said fragrance solution to contain at least one of a chelating agent, a foaming agent and mixtures thereof.

22. A room fragrance system, said system comprising:
   a plurality of absorbent sheets;
   fragrance means for imparting fragrance to said plurality of absorbent sheets, said fragrance means having a formulation comprising one of water in a range of about 15 percent to about 70 percent, a surfactant in a range of about 25 percent to about 75 percent, a fragrance in a range of about 3 percent to about 22 percent, a solvent in a range of about 1 percent to about 20 percent, a light stabilizer in a range of about 0.0001 percent to about 0.05 percent, a buffer in a range of greater than 0.0 percent to about 1.2 percent, and a preservative in a range of about 0.001 percent to about 1.1 percent;
   enclosure means for containing said plurality of absorbent sheets and said fragrance means; and
   outlet means for exposing a portion of one of said plurality of absorbent sheets to the environment wherein said outlet means has an opening sized to support one of said plurality of absorbent sheets and allows said fragrance means to permeate from said enclosure means through said exposed position of one of said plurality of absorbent sheets to said environment.

23. The room fragrance system of claim 22 wherein said outlet means has a cross-sectional surface area of about 0.19 square inches or greater.

24. The room fragrance system of claim 22 wherein said formulation further includes an antioxidant.

25. The room fragrance system of claim 22 wherein said water is in a range of about 20 percent to about 60 percent, said surfactant is in a range of about 36 percent to about 65 percent, said fragrance is in a range of about 4 percent to about 18 percent, said solvent is in a range of about 2 percent to about 10 percent, said light stabilizer is in a range of about 0.005 percent to about 0.01 percent, said buffer is in a range of greater than 0.0 percent to about 0.05 percent, said preservative is in a range of about 0.005 percent to about 1 percent, and said antioxidant is in a range of greater than 0.0 percent to about 0.05 percent.

26. The room fragrance system of claim 22 wherein said fragrance means further includes a chelating agent.

27. The room fragrance system of claim 26 wherein said chelating agent is in the range of greater than zero percent but less than or equal to a range of about 15 percent.

28. The room fragrance system of claim 27 wherein said chelating agent is in the range of greater than zero percent but less than or equal to a range of about 10 percent.

29. The room fragrance system of claim 22 wherein said fragrance means further includes a foaming agent.

30. The room fragrance system of claim 29 wherein said foaming agent is in the range of greater than zero percent but less than or equal to a range of about 15 percent.

31. The room fragrance system of claim 30 wherein said foaming agent is in the range of greater than zero percent but less than or equal to a range of about 10 percent.

* * * * *